US012612596B2

(12) United States Patent
Daub et al.

(10) Patent No.: US 12,612,596 B2
(45) Date of Patent: *Apr. 28, 2026

(54) INDUSTRIAL FERMENTATION PROCESS FOR BACILLUS USING PARTIAL HARVEST

(71) Applicant: BASF SE, Ludwigshafen (DE)

(72) Inventors: Andreas Daub, Ludwigshafen (DE); Aydin Golabgir Anbarani, Ludwigshafen (DE); Tobias Klein, Ludwigshafen (DE); Michael Morweiser, Ludwigshafen (DE); Georg Benjamin Wandrey, Ludwigshafen (DE)

(73) Assignee: BASF SE, Ludwigshafen am Rhein (DE)

( * ) Notice: Subject to any disclaimer, the term of this patent is extended or adjusted under 35 U.S.C. 154(b) by 525 days.

This patent is subject to a terminal disclaimer.

(21) Appl. No.: 18/018,112

(22) PCT Filed: Jul. 27, 2021

(86) PCT No.: PCT/EP2021/071057
§ 371 (c)(1),
(2) Date: Jan. 26, 2023

(87) PCT Pub. No.: WO2022/023371
PCT Pub. Date: Feb. 3, 2022

(65) Prior Publication Data
US 2023/0272333 A1    Aug. 31, 2023

(30) Foreign Application Priority Data
Jul. 28, 2020    (EP) ..................................... 20188161

(51) Int. Cl.
*C12R 1/07* (2006.01)
*C12N 1/205* (2026.01)

(52) U.S. Cl.
CPC .......... *C12N 1/205* (2021.05); *C12R 2001/07* (2021.05)

(58) Field of Classification Search
CPC ............................ C12N 1/205; C12R 2001/07
See application file for complete search history.

(56) References Cited

U.S. PATENT DOCUMENTS 5,698,415 A    12/1997  Jorgensen et al.
2012/0202246 A1*  8/2012  Sun ......................... C12N 15/75
                                                          435/320.1

(Continued)

FOREIGN PATENT DOCUMENTS

EP          0506780 B1 * 10/1994  ........... C12N 15/902
WO     WO-91/09129 A1    6/1991

(Continued)

OTHER PUBLICATIONS

Bogdan et al. "Bordetella pertussis Autoregulates Pertussis Toxin Production through the Metabolism of Cysteine", Nov. 2001, Infection and Immunity, vol. 69, No. 11, p. 6823-6830 (Year: 2001).*

(Continued)

*Primary Examiner* — Daniel E Kolker
*Assistant Examiner* — Amelia Nicole Dickens
(74) *Attorney, Agent, or Firm* — ArentFox Schiff LLP

(57) ABSTRACT

The present invention relates to the field of industrial fermentation. In particular, it relates to method for producing a protein of interest from a *Bacillus* host cell comprising the steps of inoculating a fermentation medium with a *Bacillus* host cell comprising an expression construct for a gene encoding a protein of interest, cultivating the *Bacillus* host cell in said fermentation medium under conditions conducive for the growth of the *Bacillus* host cell and the expression of the protein of interest for a cultivation phase, wherein the cultivation of the *Bacillus* host cell during said cultiva- (Continued)

Figure 1:
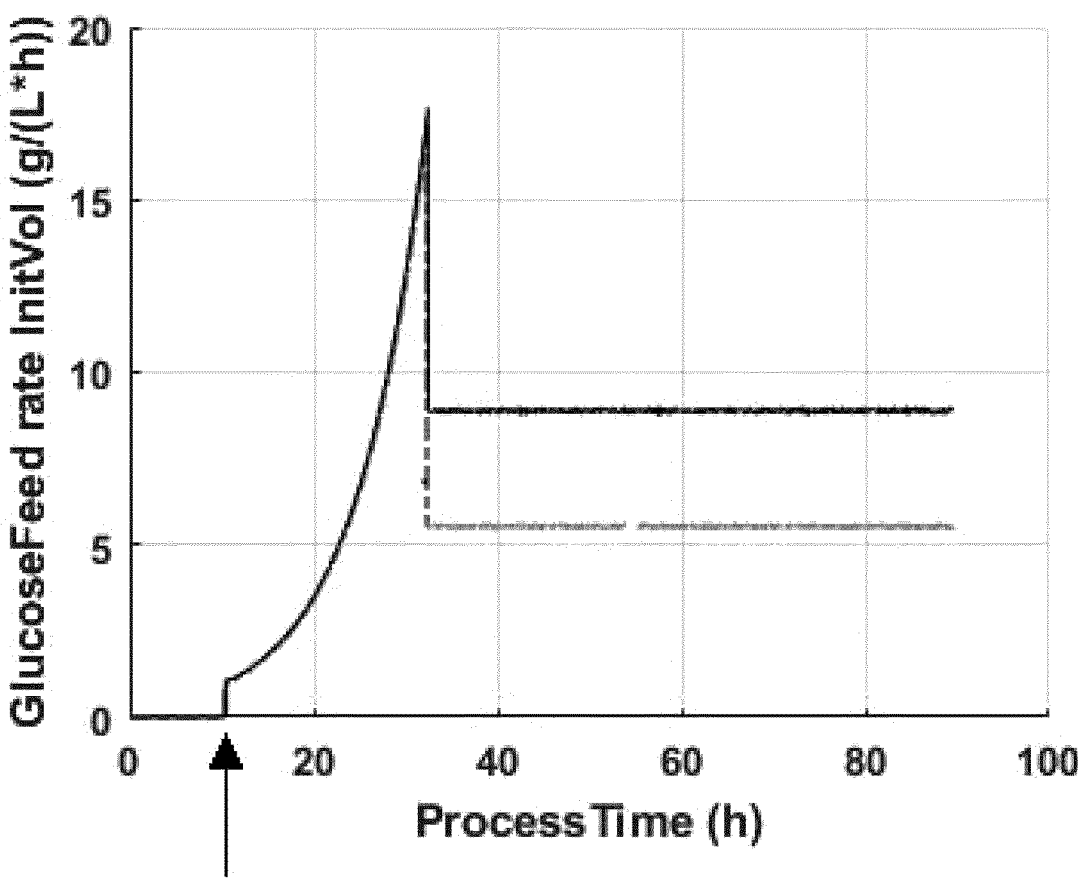

tion phase comprises the addition of at least one feed solution and wherein the at least one feed solution provides a carbon source, and separating portions from said *Bacillus* host cell culture during the cultivation phase at different time points and obtaining the protein of interest from said portions.

13 Claims, 3 Drawing Sheets

(56)　　　　　References Cited

U.S. PATENT DOCUMENTS

| | | | | |
|---|---|---|---|---|
| 2016/0168554 A1 * | 6/2016 | Messina | ............... | C12N 9/2474 |
| | | | | 435/320.1 |
| 2023/0272333 A1 * | 8/2023 | Daub | .................... | C12N 1/205 |
| | | | | 435/252.1 |

FOREIGN PATENT DOCUMENTS

| | | | | | |
|---|---|---|---|---|---|
| WO | WO-94/25612 | A2 | 11/1994 | | |
| WO | WO-99/43835 | A2 | 9/1999 | | |
| WO | WO-2004003216 | A2 * | 1/2004 | ............... | C12N 9/54 |
| WO | WO-2005/098016 | A2 | 10/2005 | | |
| WO | WO-2015/118126 | A1 | 8/2015 | | |

OTHER PUBLICATIONS

Christiansen et al. "Production of savinase and population viability of Bacillus clausii during high-cell-density fed-batch cultivations", May 28, 2003, Biotechnology and Bioengineering, vol. 83, Issue 3, pp. 344-352 (Year: 2003).*

Agaisse et al., Structural and functional analysis of the promoter region involved in full expression of the cryIIIA toxin gene of Bacillus thuringiensis, Mol. Microbiol., 13(1):97-107 (1994).

Chuen-Im et al., Production of a yeast cell wall degrading enzyme, beta-1,3-glucanase by recombinant Bacillus subtilis, Biochem. Soc. Trans., 26(2):S175 (May 1998).

Dempsey et al., Localization of the replication origin of plasmid pE194, J. Bacteriol., 171(5):2866-9 (1989).

Ehrlich et al., Plasmid replication and structural stability in Bacillus subtilis, Res. Microbiol., 142(7-8):869-73 (1991).

Ehrlich, DNA cloning in Bacillus subtilis, Proc. Natl. Acad. Sci. USA, 75(3):1433-6 (1978).

International Application No. PCT/EP2021/071057, International Search Report and Written Opinion, mailed Nov. 19, 2021.

Janniere et al., Structurally stable Bacillus subtilis cloning vectors, Gene, 87:53-6 (1990).

Stewart et al., Genes and regulatory sites of the "host-takeover module" in the terminal redundancy of Bacillus subtilis bacteriophage SPO1, Virology, 246(2):329-40 (1998).

Veith et al., The complete genome sequence of Bacillus licheniformis DSM 13, an organism with great industrial potential, J. Mol. Microbiol. Biotechnol., 7:204-11 (2004).

* cited by examiner

INDUSTRIAL FERMENTATION PROCESS FOR BACILLUS USING PARTIAL HARVEST

CROSS-REFERENCE TO RELATED APPLICATIONS

This is the U.S. national phase of International Application No. PCT/EP2021/071057, filed Jul. 27, 2021, which claims the benefit of European Patent Application No. 20188161.2, filed Jul. 28, 2020.

The present invention relates to the field of industrial fermentation. In particular, it relates to a method for producing a protein of interest from a *Bacillus* host cell comprising the steps of inoculating a fermentation medium with a *Bacillus* host cell comprising an expression construct for a gene encoding a protein of interest, cultivating the *Bacillus* host cell in said fermentation medium under conditions conducive for the growth of the *Bacillus* host cell and the expression of the protein of interest for a cultivation phase, wherein the cultivation of the *Bacillus* host cell during said cultivation phase comprises the addition of at least one feed solution and wherein the at least one feed solution provides a carbon source, and separating portions from said *Bacillus* host cell culture during the cultivation phase at different time points and obtaining the protein of interest from said portions.

Microorganisms are widely used as industrial workhorses for the production of a product of interest, especially proteins, and in particular enzymes. The biotechnological production of the product of interest is conducted via fermentation and subsequent purification of the product. Microorganisms, like the *Bacillus* species, are capable of secreting significant amounts of product into the fermentation broth. This allows a simple product purification process compared to intracellular production and explains the success of *Bacillus* in industrial application.

Industrial bioprocesses using microorganisms are typically performed in large-scale production bioreactors having a size of more than 50 m³. For the fermentation process in said large-scale bioreactors, typically, inoculation of the fermentation broth in the bioreactor is carried out with a pre-culture of *Bacillus* cells. A pre-culture can be obtained by cultivating *Bacillus* cells in smaller seed fermenters.

The large-scale fermentation process usually comprises growing the inoculated *Bacillus* cells under conditions which allow for growth and expression of the protein of interest to be produced. Typically, *Bacillus* cells are grown in complex or defined fermentation media and carbon sources will be fed in constant or varying amounts during cultivation.

Different approaches have been reported aiming at increasing the yield of protein of interest produced by the *Bacillus* cells during said cultivation in large scale bioreactors. These approaches concerned, e.g., variations in the composition of media. In carbon-limited fed-batch fermentations, the rate of carbon source addition (also names as the carbon feeding rate) determines the specific substrate uptake rate per mass of biomass and the specific growth rate of the biomass. Therefore, other approaches concerned increase of specific substrate uptake and growth rates.

However, means for further increasing yield in large-scale industrial fermentation processes are highly desired.

The technical problem underlying the present invention may be seen as the provision of means and methods for complying with the aforementioned needs. It can be solved by the embodiments characterized in the claims and herein below.

Thus, the present invention relates to a method for producing a protein of interest from a *Bacillus* host cell comprising the steps of:

(a) inoculating a fermentation medium with a *Bacillus* host cell comprising an expression construct for a gene encoding a protein of interest;

(b) cultivating the *Bacillus* host cell in said fermentation medium under conditions conducive for the growth of the *Bacillus* host cell and the expression of the protein of interest for a cultivation phase, wherein the cultivation of the *Bacillus* host cell during said cultivation phase comprises the addition of at least one feed solution and wherein the at least one feed solution provides a carbon source; and (c) separating portions from said *Bacillus* host cell culture during the cultivation phase at different time points and obtaining the protein of interest from said portions.

It is to be understood that as used in the specification and in the claims, "a" or "an" can mean one or more, depending upon the context in which it is used. Thus, for example, reference to "a cell" can mean that at least one cell can be utilized.

Further, it will be understood that the term "at least one" as used herein means that one or more of the items referred to following the term may be used in accordance with the invention. For example, if the term indicates that at least one feed solution shall be used this may be understood as one feed solution or more than one feed solutions, i.e. two, three, four, five or any other number of feed solutions. Depending on the item the term refers to the skilled person understands as to what upper limit the term may refer, if any.

The term "about" as used herein means that with respect to any number recited after said term an interval accuracy exists within in which a technical effect can be achieved. Accordingly, about as referred to herein, preferably, refers to the precise numerical value or a range around said precise numerical value of ±20%, preferably ±15%, more preferably ±10%, or even more preferably ±5%.

The term "comprising" as used herein shall not be understood in a limiting sense. The term rather indicates that more than the actual items referred to may be present, e.g., if it refers to a method comprising certain steps, the presence of further steps shall not be excluded. However, the term also encompasses embodiments where only the items referred to are present, i.e. it has a limiting meaning in the sense of "consisting of".

The present invention, thus, provides for a method that can be applied for producing a protein of interest from a *Bacillus* host cell culture. The method, in particular comprises culturing *Bacillus* host cells. This can be done in both, laboratory and industrial scale fermentation processes.

"Industrial fermentation" as referred to in accordance with the present invention refers to a cultivation method in which at least 200 g of a carbon source per liter of initial fermentation medium will be added.

The method according to the present invention may also comprise further steps. Such further steps may encompass further steps of treating the protein of interest obtained from the *Bacillus* host cell culture or steps of relating to cultivation.

The term "producing" as used herein refers to expressing the protein of interest in the *Bacillus* host cell culture from the expression construct. Moreover, the term may also comprise obtaining the said protein of interest from the *Bacillus* host cell culture. Accordingly, the method of the invention may, thus, be applied for manufacturing the protein of interest.

The term "cultivating" or "cultivation" as used herein refers to keeping alive and/or propagating *Bacillus* cells comprised in a culture at least for a predetermined time. The term encompasses phases of exponential cell growth at the beginning of growth after inoculation as well as phases of stationary growth.

In the method of the present invention, a fermentation medium is inoculated with a *Bacillus* host cell comprising an expression construct for a gene encoding a protein of interest as a first step.

The term "inoculating" as used herein refers to introducing *Bacillus* host cells into the fermentation medium used cultivation. Inoculation of the fermentation medium with the *Bacillus* host cells can be achieved by introducing *Bacillus* host cells of a pre-culture (starter culture). Preferably, the fermentation is inoculated with pre-culture that has been grown under conditions known to the person skilled in the art. The pre-culture can be obtained by cultivating the cells in a pre-culture medium that can be a chemically defined pre-culture medium or a complex pre-culture medium. The pre-culture medium can be the same or different from the fermentation medium used for cultivation in the method of the present invention. The complex pre-culture medium can contain complex nitrogen and/or complex carbon sources. Preferably, the pre-culture used for inoculation is obtained by using a complex culture medium. The pre-culture can be added all or in part to the main fermentation medium. Preferably, the *Bacillus* host cells in the pre-culture are actively growing cells, i.e. they are in a stage where the number of cells is increasing. Typically, cells in a pre-culture are upon inoculation of the pre-culture in a lag phase and switch over time to a phase of exponential growth. Preferably, cells in the exponential growth phase are used for from the pre-culture for inoculation of the fermentation medium. The volume ratio between pre-culture used for inoculation and main fermentation medium is, preferably, between 0.1 and 30% (v/v).

The term "*Bacillus* host cell" refers to a *Bacillus* cell which serves as a host for an expression construct for a gene encoding a protein of interest. Said expression construct may be a naturally occurring expression construct, a recombinantly introduced expression construct or a naturally occurring expression construct which has been genetically modified in the *Bacillus* cell. The *Bacillus* host cell may be a host cell from any member of the bacterial genus *Bacillus*, preferably a host cell of *Bacillus licheniformis, Bacillus subtilis, Bacillus alkalophilus, Bacillus amyloliquefaciens, Bacillus brevis, Bacillus circulans, Bacillus clausii, Bacillus coagulans, Bacillus firmus, Bacillus jautus, Bacillus lentus, Bacillus megaterium, Bacillus pumilus, Bacillus stearothermophilus, Bacillus thuringiensis* or *Bacillus velezensis*. More preferably, the *Bacillus* host cell is a *Bacillus licheniformis, Bacillus pumilus*, or *Bacillus subtilis* host cell, even more preferred *Bacillus licheniformis* or *Bacillus subtilis* host cell, most preferably, *Bacillus licheniformis* host cell. Particular preferably, the *Bacillus licheniformis* is selected from the group consisting of *Bacillus licheniformis* as deposited under American Type Culture Collection number ATCC 14580, ATCC 31972, ATCC 53926, ATCC 53757, ATCC 55768, and under DSMZ number (German Collection of Microorganisms and Cell Cultures GmbH) DSM 13, DSM 394, DSM 641, DSM 1913, DSM 11259, and DSM 26543.

Typically, the host cell belongs to the species *Bacillus licheniformis*, such as a host cell of the *Bacillus licheniformis* strain as deposited under American Type Culture Collection number ATCC 14580 (which is the same as DSM 13, see Veith et al. "The complete genome sequence of *Bacillus licheniformis* DSM 13, an organism with great industrial potential." J. Mol. Microbiol. Biotechnol. (2004) 7:204-211). Alternatively, the host cell may be a host cell of *Bacillus licheniformis* strain ATCC 53926. Alternatively, the host cell may be a host cell of *Bacillus licheniformis* strain ATCC 31972. Alternatively, the host cell may be a host cell of *Bacillus licheniformis* strain ATCC 53757. Alternatively, the host cell may be a host cell of *Bacillus licheniformis* strain ATCC 53926. Alternatively, the host cell may be a host cell of *Bacillus licheniformis* strain ATCC 55768. Alternatively, the host cell may be a host cell of *Bacillus licheniformis* strain DSM 394. Alternatively, the host cell may be a host cell of *Bacillus licheniformis* strain DSM 641. Alternatively, the host cell may be a host cell of *Bacillus licheniformis* strain DSM 1913. Alternatively, the host cell may be a host cell of *Bacillus licheniformis* strain DSM 11259. Alternatively, the host cell may be a host cell of *Bacillus licheniformis* strain DSM 26543.

Preferably, the *Bacillus licheniformis* strain is selected from the group consisting of *Bacillus licheniformis* ATCC 14580, ATCC 31972, ATCC 53757, ATCC 53926, ATCC 55768, DSM 13, DSM 394, DSM 641, DSM 1913, DSM 11259, and DSM 26543.

The *Bacillus* host cell to be applied in the method of the present invention shall comprise an expression construct for a gene encoding a protein of interest to be expressed by the said host cell. The term "expression construct" as referred to herein refers to a polynucleotide comprising a nucleic acid sequence encoding the protein of interest operably linked to an expression control sequence, e.g., a promoter. A promoter as referred to herein is a nucleotide sequence located upstream of a gene on the same strand as the gene that enables transcription of said gene. The promoter is followed by the transcription start site of the gene. The promoter is recognized by an RNA polymerase, typically, together with the required transcription factors, which initiate transcription. A functional fragment or functional variant of a promoter is a nucleotide sequence which is recognizable by RNA polymerase and is capable of initiating transcription. Functional fragments or functional variants of promoters are also encompassed as a promoter in the sense of the present invention. Promoters may be inducer-dependent promoters the activity of which depend on an activating signal molecule, i.e., the presence of an inducer molecule, or may be inducer-independent promoters, i.e. promoters that do not depend on the presence of an inducer molecule added to the fermentation medium and that are either constitutively active or can be increased in activity regardless of the presence of an inducer molecule that is added to the fermentation medium.

Preferably, the promoter is selected from the group consisting of the promoter sequences of the aprE promoter (a native promoter from the gene encoding the *Bacillus* subtilisin Carlsberg protease), amyQ promoter from *Bacillus amyloliquefaciens*, amyL promoter and variants thereof from *Bacillus licheniformis* (preferably as de-scribed in U.S. Pat. No. 5,698,415), bacteriophage SPO1 promoter, preferably the promoter P4, P5, or P15 (preferably as described in WO2015118126 or in Stewart, C. R., Gaslightwala, I., Hinata, K., Krolikowski, K. A., Needleman, D. S., Peng, A. S., Peterman, M. A., Tobias, A., and Wei, P. 1998, Genes and regulatory sites of the "host-takeover module" in the terminal redundancy of *Bacillus subtilis* bacteriophage SPO1. Virology 246(2), 329-340), cryIIIA promoter from *Bacillus thuringiensis* (preferably as described in WO9425612 or in Agaisse, H. and Lereclus, D. 1994. Structural and functional analysis of the promoter region involved in full expression of the cryIIIA toxin gene of *Bacillus thuringiensis*. Mol. Microbiol. 13(1). 97-107.), and combinations thereof, and active fragments or variants thereof. Preferably, the promoter sequences can be combined with 5'-UTR sequences native or heterologous to the host cell, as described herein. Preferably, the promoter is selected from the group consisting of: an veg promoter, lepA promoter, serA promoter, ymdA promoter, fba promoter, aprE promoter, amyQ promoter, amyL promoter, bacteriophage SPO1 promoter, cryIIIA promoter, combinations thereof, and active fragments or variants thereof. More preferably, the promoter sequence is selected from the group consisting of aprE promoter, amyL promoter, veg promoter, bacteriophage SPO1 promoter, and cryIIIA promoter, and combinations thereof, or active fragments or variants thereof. More preferably, the promoter is selected from the group consisting of: an aprE promoter, SPO1 promoter, preferably P4, P5, or P15 (preferably as described in WO15118126), tandem promoter comprising the promoter sequences amyl and amyQ (preferably as described in WO9943835), and triple promoter comprising the promoter sequences amyL, amyQ, and cryIIIa (preferably as described in WO2005098016). Most preferably, the promoter is an aprE promoter, preferably, an aprE promoter from *Bacillus amyloliquefaciens*, *Bacillus clausii*, *Bacillus haloduans*, *Bacillus lentus*, *Bacillus licheniformis*, *Bacillus pumilus*, *Bacillus subtilis*, or *Bacillus velezensis*, more preferably from *Bacillus licheniformis*, *Bacillus pumilus* or *Bacillus subtilis*, most preferably, from *Bacillus licheniformis*.

It will be understood that the activity of the promoter used in accordance with the method of the present invention, preferably, is not dependent on heat-inducible elements. Accordingly, the promoter to be used as an expression control sequence in accordance of the present invention, preferably, is a temperature-insensitive promoter and/or lacks a heat-inducible element.

Moreover, said expression construct may comprise further elements required for proper termination of translation or elements required for insertion, stabilization, introduction into a host cell or replication of the said expression construct. Such sequences encompass, inter alia, 5'-UTR (also called leader sequence), ribosomal binding site (RBS, Shine-Dalgarno sequence), 3'-UTR, transcription start and stop sites and, depending on the nature of the expression construct, origin of replications, integration sites, and the like. Preferably, the nucleic acid construct and/or the expression vector comprises a 5'-UTR and a RBS. Preferably, the 5'-UTR is selected from the control sequence of a gene selected from the group consisting of aprE, grpE, ctoG, SP82, gsiB, cryIIa and ribG gene.

Yet, the expression construct shall also comprise a nucleic acid sequence encoding a protein of interest. The "protein of interest" as referred to herein refers to any protein, peptide or fragment thereof which is intended to be produced in the *Bacillus* host cell. A protein, thus, encompasses polypeptides, peptides, fragments thereof as well as fusion proteins and the like.

Preferably, the protein of interest is an enzyme. In a particular embodiment, the enzyme is classified as an oxidoreductase (EC 1), a transferase (EC 2), a hydrolase (EC 3), a lyase (EC 4), an isomerase (EC 5), or a ligase (EC 6) (EC-numbering according to Enzyme Nomenclature, Recommendations (1992) of the Nomenclature Committee of the International Union of Biochemistry and Molecular Biology including its supplements published 1993-1999). In a preferred embodiment, the protein of interest is an enzyme suitable to be used in detergents.

Most preferably, the enzyme is a hydrolase (EC 3), preferably, a glycosidase (EC 3.2) or a peptidase (EC 3.4). Especially preferred enzymes are enzymes selected from the group consisting of an amylase (in particular an alpha-amylase (EC 3.2.1.1)), a cellulase (EC 3.2.1.4), a lactase (EC 3.2.1.108), a mannanase (EC 3.2.1.25), a lipase (EC 3.1.1.3), a phytase (EC 3.1.3.8), a nuclease (EC 3.1.11 to EC 3.1.31), and a protease (EC 3.4); in particular an enzyme selected from the group consisting of amylase, protease, lipase, mannanase, phytase, xylanase, phosphatase, glucoamylase, nuclease, and cellulase, preferably, amylase or protease, preferably, a protease. Most preferred is a serine protease (EC 3.4.21), preferably a subtilisin protease.

It will be understood that each of the expression control sequence, nucleic acid sequence encoding the protein of interest and/or the aforementioned further elements may be from the *Bacillus* host cell or may be from another species, i.e. heterologous with respect to said *Bacillus* host cell.

Further, the expression construct may be an arrangement of a gene of interest and the expression control sequence and/or further elements as specified before which is native to, i.e., endogenously present in the genome of the *Bacillus* host cell. Moreover, the term also encompasses such native expression constructs which have been genetically manipulated, e.g., by genomic editing and/or mutagenesis technologies.

The expression construct may also be an exogenously introduced expression construct. In an exogenously introduced expression construct, the expression control sequence, the gene encoding the protein of interest and/or the further elements may be native with respect to the host cell or may be derived from other species, i.e. be heterologous with respect to the *Bacillus* host cell. The introduction of the expression construct into a *Bacillus* host cell can be accomplished in accordance with the present invention by any method known in the art, including, inter alia, well known transformation, transfection, transduction, and conjugation techniques and the like. Preferably, the expression construct exogenously introduced is comprised in a vector, preferably, an expression vector. The expression vector can be, preferably, located outside the chromosomal DNA of the *Bacillus* host cell, i.e. be present episomally, in one or more copies. However, the expression vector may also preferably be integrated into the chromosomal DNA of the *Bacillus* cell in one or more copies. The expression vector can be linear or circular. Preferably, the expression vector is a viral vector or a plasmid.

For autonomous replication, the expression vector may further comprise an origin of replication enabling the vector to replicate autonomously in the host cell in question. Bacterial origins of replication include but are not limited to the origins of replication of plasmids pUB110, pC194, pTB19, pAM131, and pTA1060 permitting replication in *Bacillus* (Janniere, L., Bruand, C., and Ehrlich, S. D. (1990). Structurally stable *Bacillus subtilis* cloning vectors. Gene 87, 53-6; Ehrlich, S. D., Bruand, C., Sozhamannan, S., Dabert, P., Gros, M. F., Janniere, L., and Gruss, A. (1991). Plasmid replication and structural stability in *Bacillus subtilis*. Res. Microbiol. 142, 869-873), and pE194 (Dempsey, L. A. and Dubnau, D. A. (1989). Localization of the replication origin of plasmid pE194. J. Bacteriol. 171, 2866-2869). The origin of replication may be one having a mutation to make its function temperature-sensitive in the host cell (see, e.g., Ehrlich, 1978, Proceedings of the National Academy of Sciences USA 75:1433-1436). Yet, the expression vector, preferably, contains one or more selectable markers that permit easy selection of transformed *Bacillus* host cells. A selectable marker is a gene encoding a product, which provides for biocide resistance, resistance to heavy metals, prototrophy to auxotrophs, and the like. Bacterial selectable markers include but are not limited to the dal genes from *Bacillus subtilis* or *Bacillus licheniformis*, or markers that confer antibiotic resistance such as ampicillin, kanamycin, erythromycin, chloramphenicol or tetracycline resistance. Furthermore, selection may be accomplished by co-transformation, e.g., as described in WO9109129, where the selectable marker is on a separate vector.

The term "cultivation phase" as used herein refers to a period of time for which cultivation is to be carried out under addition of at least one feed solution. Said at least one feed solution provides a carbon source. The carbon source may be provided, preferably, at constant or varying rates, typically at increasing rates, during the cultivation phase. Particular preferred profiles for providing the carbon source envisaged in accordance with the present invention are described elsewhere herein. Moreover, during the cultivation phase, conditions are applied to the culture which are conducive for the growth of the *Bacillus* host cell and the expression of the protein of interest. Preferred conditions are described elsewhere herein in detail.

The *Bacillus* host cell culture is, preferably, depleted from the at least one carbon source after inoculation of the fermentation medium and prior to the first cultivation phase. This can be achieved by cultivation techniques well known to the skilled artisan. Preferably, the depletion can be detected by observing a sudden rise in the dissolved oxygen value provided by a sensor or a rise in pH. More preferably, depletion is characterized by a rise of dissolved oxygen (DO) of at least 10% and/or a rise of pH of at least 0.1 units. Also preferably, depletion can be achieved by inoculation with a pre-culture in which most of the carbon source has been consumed by cultivation to a volume at least 3.33 times larger than said pre-culture volume.

The term "fermentation medium" as used herein refers to a water-based solution containing one or more chemical compounds that can support the growth of cells. Preferably, the fermentation medium according to the present invention is a complex fermentation medium or a chemically defined fermentation medium.

A complex fermentation medium as used to herein refers to a fermentation medium that comprise a complex nutrient source in an amount of 0.5 to 30% (w/v) of the fermentation medium. Complex nutrient sources are nutrient sources which are composed of chemically undefined compounds, i.e., compounds that are not known by their chemical formula, preferably comprising undefined organic nitrogen- and/or carbon-containing compounds. In contrast thereto, a "chemically defined nutrient source" (e.g., "chemically defined carbon source" or "chemically defined nitrogen source") is understood to be used for nutrient sources which are composed of chemically defined compounds. A chemically defined component is a component which is known by its chemical formula. A complex nitrogen source is a nutrient source that is composed of one or more chemically undefined nitrogen containing compounds, i.e., nitrogen containing compounds that are not known by their chemical formula, preferably comprising organic nitrogen containing compounds, e.g., proteins and/or amino acids with unknown composition. A complex carbon source is a carbon source that is composed of one or more chemically undefined carbon containing compounds, i.e., carbon containing compounds that are not known by their chemical formula, preferably comprising organic carbon containing compounds, e.g., carbohydrates with unknown composition. It is clear for the skilled person that a complex nutrient source might be a mixture of different complex nutrient sources. Thus, a complex nitrogen source can comprise a complex carbon source and vice versa and a complex nitrogen source can be metabolized by the cells in a way that it functions as carbon source and vice versa.

Preferably, the complex nutrient source is a complex nitrogen source. Complex sources of nitrogen include, but are not limited to protein-containing substances, such as an extract from microbial, animal or plant cells, e.g., plant protein preparations, soy meal, corn meal, pea meal, corn gluten, cotton meal, peanut meal, potato meal, meat, casein, gelatins, whey, fish meal, yeast protein, yeast extract, tryptone, peptone, bacto-tryptone, bacto-peptone, wastes from the processing of microbial cells, plants, meat or animal bodies, and combinations thereof. In one embodiment, the complex nitrogen source is selected from the group consisting of plant protein, preferably potato protein, soy protein, corn protein, peanut, cotton protein, and/or pea protein, casein, tryptone, peptone and yeast extract and combinations thereof.

Preferably, the fermentation medium may also comprise defined media components. Preferably, the fermentation medium also comprises a defined nitrogen source. Examples of inorganic nitrogen sources are ammonium, nitrate, and nitrite, and combinations thereof. In a preferred embodiment, the fermentation medium comprises a nitrogen source, wherein the nitrogen source is a complex or a defined nitrogen source or a combination thereof. In one embodiment, the defined nitrogen source is selected from the group consisting of ammonia, ammonium, ammonium salts, (e.g., ammonium chloride, ammonium nitrate, ammonium phosphate, ammonium sulfate, ammonium acetate), urea, nitrate, nitrate salts, nitrite, and amino acids, preferably, glutamate, and combinations thereof.

Preferably, the complex nutrient source is in an amount of 2 to 15% (v/w) of the fermentation medium. In another embodiment, the complex nutrient source is in an amount of 3 to 10% (v/w) of the fermentation medium.

Also preferably, the complex fermentation medium may further comprise a carbon source. The carbon source is, preferably, a complex or a defined carbon source or a combination thereof. Preferably, the complex nutrient source comprises a carbohydrate source. Various sugars and sugar-containing substances are suitable sources of carbon, and the sugars may be present in different stages of polymerization. Preferred complex carbon sources to be used in the present invention are selected from the group consisting of molasse, corn steep liquor, cane sugar, dextrin, starch, starch hydrolysate, and cellulose hydrolysate, and combinations thereof. Preferred defined carbon sources are selected from the group consisting of carbohydrates, organic acids, and alcohols, preferably, glucose, fructose, galactose, xylose, arabinose, sucrose, maltose, lactose, acetic acid, propionic acid, lactic acid, formic acid, malic acid, citric acid, fumaric acid, glycerol, inositol, mannitol and sorbitol, and combinations thereof. Preferably, the defined carbon source is provided in form of a syrup, which can comprise up to 20%, preferably, up to 10%, more preferably up to 5% impurities. In one embodiment, the carbon source is sugar beet syrup, sugar cane syrup, corn syrup, preferably, high fructose corn syrup. In another embodiment, the complex carbon source is selected from the group consisting of molasses, corn steep liquor, dextrin, and starch, or combinations thereof, and wherein the defined carbon source is selected from the group consisting of glucose, fructose, galactose, xylose, arabinose, sucrose, maltose, dextrin, lactose, or combinations thereof.

Preferably, the fermentation medium is a complex medium comprising complex nitrogen and complex carbon sources. More preferably, the fermentation medium is a complex medium comprising complex nitrogen and carbon sources, wherein the complex nitrogen source may be partially hydrolyzed as described in WO 2004/003216.

Yet, the fermentation medium may, typically, also comprises a hydrogen source, an oxygen source, a sulfur source, a phosphorus source, a magnesium source, a sodium source, a potassium source, a trace element source, and a vitamin source as further described elsewhere herein.

In another embodiment, the fermentation medium may be a chemically defined fermentation medium. A chemically defined fermentation medium is a fermentation medium which is essentially composed of chemically defined components in known concentrations. A chemically defined component is a component which is known by its chemical formula. A fermentation medium which is essentially composed of chemically defined component includes a medium which does not contain a complex nutrient source, in particular, no complex carbon and/or complex nitrogen source, i.e., which does not contain complex raw materials having a chemically undefined composition. A fermentation medium which is essentially composed of chemically defined components may further include a medium which comprises an essentially small amount of a complex nutrient source, for instance a complex nitrogen and/or carbon source, an amount as defined below, which typically is not sufficient to maintain growth of the *Bacillus* host cells and/or to guarantee formation of a sufficient amount of biomass.

In that regard, complex raw materials have a chemically undefined composition due to the fact that, for instance, these raw materials contain many different compounds, among which complex heteropolymeric compounds, and have a variable composition due to seasonal variation and differences in geographical origin. Typical examples of complex raw materials functioning as a complex carbon and/or nitrogen source in fermentation are soybean meal, cotton seed meal, corn steep liquor, yeast extract, casein hydrolysate, molasses, and the like. An essentially small amount of a complex carbon and/or nitrogen source may be present in the chemically defined fermentation medium according to the invention, for instance as carry-over from the inoculum for the main fermentation. The inoculum for the main fermentation is not necessarily obtained by fermentation on a chemically defined medium. Most often, carry-over from the inoculum will be detectable through the presence of a small amount of a complex nitrogen source in the chemically defined fermentation medium of the main fermentation. Small amounts of a complex medium components, like complex carbon and/or nitrogen source, might also be introduced into the fermentation medium by the addition of small amounts of these complex components to the fermentation medium. It may be advantageous to use a complex carbon and/or nitrogen source in the fermentation process of the inoculum for the main fermentation, for instance to speed up the formation of biomass. i.e. to increase the growth rate of the microorganism, and/or to facilitate internal pH control. For the same reason, it may be advantageous to add an essentially small amount of a complex carbon and/or nitrogen source, e.g. yeast extract, to the initial stage of the main fermentation, especially to speed up biomass formation in the early stage of the fermentation process. An essentially small amount of a complex nutrient source which may be added to the chemically defined fermentation medium in the fermentation process according to the invention is defined to be an amount of at the most 10% of the total amount of the respective nutrient, which is added in the fermentation process. In particular, an essentially small amount of a complex carbon and/or nitrogen source which may be added to the chemically defined fermentation medium is defined to be an amount of a complex carbon source resulting in at the most 10% of the total amount of carbon and/or an amount of a complex nitrogen source resulting in at the most 10% of the total amount of nitrogen, which is added in the fermentation process, preferably an amount of a complex carbon source resulting in at the most 5% of the total amount of carbon and/or an amount of a complex nitrogen source resulting in at the most 5% of the total amount of nitrogen, more preferably an amount of a complex carbon source resulting in at the most 1% of the total amount of carbon and/or an amount of a complex nitrogen source resulting in at the most 1% of the total amount of nitrogen, which is added in the fermentation process. Preferably, at the most 10% of the total amount of carbon and/or at the most 10% of the total amount of nitrogen, preferably an amount of at the most 5% of the total amount of carbon and/or an amount of at the most 5% of the total amount of nitrogen, more preferably an amount of at the most 1% of the total amount of carbon and/or an amount of at the most 1% of the total amount of nitrogen which is added in the fermentation process is added via carry-over from the inoculum. Most preferably, no complex carbon and/or complex nitrogen source is added to the fermentation medium in the fermentation process.

A chemically defined nutrient source as referred to herein e.g., chemically defined carbon source or chemically defined nitrogen source, is understood to be used for nutrient sources which are composed of chemically defined compounds.

Culturing a microorganism in a chemically defined fermentation medium requires that cells be cultured in a medium which contain various chemically defined nutrient sources selected from the group consisting of chemically defined hydrogen source, chemically defined oxygen source, chemically defined carbon source, chemically defined nitrogen source, chemically defined sulfur source, chemically defined phosphorus source, chemically defined magnesium source, chemically defined sodium source, chemically defined potassium source, chemically defined trace element source, and chemically defined vitamin source. Preferably, the chemically defined carbon source is selected from the group consisting of carbohydrates, organic acids, hydrocarbons, alcohols and mixtures thereof. Preferred carbohydrates are selected from the group consisting of glucose, fructose, galactose, xylose, arabinose, sucrose, maltose, maltotriose, lactose, dextrin, maltodextrins, starch and inulin, and mixtures thereof. Preferred alcohols are selected from the group consisting of glycerol, methanol and ethanol, inositol, mannitol and sorbitol and mixtures thereof. Preferred organic acids are selected from the group consisting of acetic acid, propionic acid, lactic acid, formic acid, malic acid, citric acid, fumaric acid and higher alkanoic acids and mixtures thereof. Preferably, the chemically defined carbon source comprises glucose or sucrose. More preferably, the chemically defined carbon source comprises glucose, even more preferably the predominant amount of the chemically defined carbon source is provided as glucose.

Most preferably, the chemically defined carbon source is glucose. It is to be understood that the chemically defined carbon source can be provided in form of a syrup, preferably as glucose syrup. As understood herein, glucose as referred to herein shall include glucose syrups. A glucose syrup is a viscous sugar solution with high sugar concentration. The sugars in glucose syrup are mainly glucose and to a minor extent also maltose and maltotriose in varying concentrations depending on the quality grade of the syrup. Preferably, besides glucose, maltose and maltotriose the syrup can comprise up to 10%, preferably, up to 5%, more preferably up to 3% impurities. Preferably, the glucose syrup is from corn.

The chemically defined nitrogen source is preferably selected from the group consisting of urea, ammonia, nitrate, nitrate salts, nitrite, ammonium salts such as ammonium chloride, ammonium sulphate, ammonium acetate, ammonium phosphate and ammonium nitrate, and amino acids such as glutamate or lysine and combinations thereof. More preferably, a chemically defined nitrogen source is selected from the group consisting of ammonia, ammonium sulphate and ammonium phosphate. Most preferably, the chemically defined nitrogen source is ammonia.

The use of ammonia as a chemically defined nitrogen source has the advantage that ammonia additionally can function as a pH controlling agent.

Additional compounds can be added in complex and chemically defined fermentation medium as described below.

Oxygen is usually provided during the cultivation of the cells by aeration of the fermentation media by stirring and/or gassing. Hydrogen is usually provided due to the presence of water in the aqueous fermentation medium. However, hydrogen and oxygen are also contained within the carbon and/or nitrogen source and can be provided that way.

Magnesium can be provided to the fermentation medium by one or more magnesium salts, preferably selected from the group consisting of magnesium chloride, magnesium sulfate, magnesium nitrate, magnesium phosphate, and combinations thereof, or by magnesium hydroxide, or by combinations of one or more magnesium salts and magnesium hydroxide.

Sodium can be added to the fermentation medium by one or more sodium salts, preferably selected from the group consisting of sodium chloride, sodium nitrate, sodium sulphate, sodium phosphate, sodium hydroxide, and combinations thereof.

Calcium can be added to the fermentation medium by one or more calcium salts, preferably selected from the group consisting of calcium sulphate, calcium chloride, calcium nitrate, calcium phosphate, calcium hydroxide, and combinations thereof.

Potassium can be added to the fermentation medium in chemically defined form by one or more potassium salts, preferably selected from the group consisting of potassium chloride, potassium nitrate, potassium sulphate, potassium phosphate, potassium hydroxide, and combinations thereof.

Phosphorus can be added to the fermentation medium by one or more salts comprising phosphorus, preferably selected from the group consisting of potassium phosphate, sodium phosphate, magnesium phosphate, phosphoric acid, and combinations thereof. Preferably, at least 1 g of phosphorus is added per liter of initial fermentation medium.

Sulfur can be added to the fermentation medium by one or more salts comprising sulfur, preferably selected from the group consisting of potassium sulfate, sodium sulfate, magnesium sulfate, sulfuric acid, and combinations thereof.

Preferably, the fermentation medium and/or the initial fermentation medium, comprises one or more selected from the group consisting of:

0.1 to 50 g nitrogen per liter of fermentation medium;
1 to 6 g phosphorus per liter of fermentation medium;
0.15 to 2 g sulfur per liter of fermentation medium;
0.4 to 8 g potassium per liter of fermentation medium;
0.01 to 2 g sodium per liter of fermentation medium;
0.01 to 3 g calcium per liter of fermentation medium; and
0.1 to 10 g magnesium per liter of fermentation medium.

Typically, the feed solution differs from the fermentation medium and/or from the initial fermentation medium, in one or more of the compounds of said group listed above. Even more typically, the feed solution differs from the fermentation medium and/or from the initial fermentation medium, in the amount of one or more of the compounds of said group listed above.

One or more trace element ions can be added to the fermentation medium, preferably in amounts of below 10 mmol/L initial fermentation medium each. These trace element ions are selected from the group consisting of iron, copper, manganese, zinc, cobalt, nickel, molybdenum, selenium, and boron and combinations thereof. Preferably, the trace element ions iron, copper, manganese, zinc, cobalt, nickel, and molybdenum are added to the fermentation medium. Preferably, the one or more trace element ions are added to the fermentation medium in an amount selected from the group consisting of 50 μmol to 5 mmol per liter of initial medium of iron, 40 μmol to 4 mmol per liter of initial medium copper, 30 μmol to 3 mmol per liter of initial medium manganese, 20 μmol to 2 mmol per liter of initial medium zinc, 1 μmol to 100 μmol per liter of initial medium cobalt, 2 μmol to 200 μmol per liter of initial medium nickel, and 0.3 μmol to 30 μmol per liter of initial medium molybdenum, and combinations thereof. For adding each trace element preferably one or more from the group consisting of chloride, phosphate, sulphate, nitrate, citrate and acetate salts can be used.

Compounds which may optionally be included in the fermentation medium are chelating agents, such as citric acid, MGDA, NTA, or GLDA, and buffering agents such as mono- and dipotassium phosphate, calcium carbonate, and the like. Buffering agents preferably are added when dealing with processes without an external pH control. In addition, an antifoaming agent may be dosed prior to and/or during the fermentation process.

Vitamins refer to a group of structurally unrelated organic compounds, which are necessary for the normal metabolism of cells. Cells are known to vary widely in their ability to synthesize the vitamins they require. A vitamin should be added to the fermentation medium of *Bacillus* cells not capable of synthesizing said vitamin. Vitamins can be selected from the group of thiamin, riboflavin, pyridoxal, nicotinic acid or nicotinamide, pantothenic acid, cyanocobalamin, folic acid, biotin, lipoic acid, purines, pyrimidines, inositol, choline and hemins.

Preferably, the fermentation medium also comprises a selection agent, e.g., an antibiotic, such as ampicillin, tetracycline, kanamycin, hygromycin, bleomycin, chloramphenicol, streptomycin or phleomycin, to which the selectable marker of the cells provides resistance.

The amount of necessary compounds to be added to the medium will mainly depend on the amount of biomass which is to be formed in the fermentation process. The amount of biomass formed may vary widely, typically the amount of biomass is from about 10 to about 150 grams of dry cell mass per liter of fermentation broth. Usually, for protein production, fermentations producing an amount of biomass which is lower than about 10 g of dry cell mass per liter of fermentation broth are not considered industrially relevant.

The optimum amount of each component of a defined medium, as well as which compounds are essential and which are non-essential, will depend on the type of *Bacillus* cell which is subjected to fermentation in a medium, on the amount of biomass and on the product to be formed. Typically, the amount of medium components necessary for growth of the microbial cell may be determined in relation to the amount of carbon source used in the fermentation, since the amount of biomass formed will be primarily determined by the amount of carbon source used.

Particular preferred fermentation media are also described in the Examples below.

Preferably, the fermentation medium is sterilized prior to use in order to prevent or reduce growth of microorganisms during the fermentation process, which are different from the inoculated microbial cells. Sterilization can be performed with methods known in the art, for example but not limited to, autoclaving or sterile filtration. Some or all medium components can be sterilized separately from other medium components to avoid interactions of medium components during sterilization treatment or to avoid decomposition of medium components under sterilization conditions.

The phrase "conditions conducive for the growth of the *Bacillus* host cell and the expression of the protein of interest" means that conditions other than the temperature or fermentation medium used for cultivation. Such conditions comprise pH during cultivation, physical movement of the culture by shaking or stirring and/or atmospheric conditions applied to the culture.

The pH of the fermentation medium during cultivation may be adjusted or maintained. Preferably, the pH of the medium is adjusted prior to inoculation. Preferred pH values envisaged for the fermentation medium are within the range of about pH 6.6 to about pH 9, preferably within the range of about pH 6.6 to about pH 8.5, more preferably within the range of about pH 6.8 to about pH 8.5, most preferably within the range of about pH 6.8 to about pH 8.0. As an example, for a *Bacillus* cell host cell culture, the pH is, preferably, adjusted to or above about pH 6.8, about pH 7.0, about pH 7.2, about pH 7.4, or about pH 7.6. Preferably, the pH of the fermentation medium during cultivation of the *Bacillus* host cell culture is adjusted to a pH within the rage of about pH 6.8 to about pH 9, preferably about pH 6.8 to about pH 8.5, more preferably about pH 7.0 to about pH 8.5, most preferably about pH 7.2 to about pH 8.0.

Physical movement can be applied by stirring and/or shaking of the fermentation medium. Preferably, said stirring of the fermentation medium is carried out with about 50 to about 2000 rpm, preferably with about 50 to about 1600 rpm, further preferred with about 800 to about 1400 rpm, more preferably with about 50 to about 200 rpm.

Besides stirring, oxygen and/or other gases may be applied to the culture by adjusting suitable atmospheric conditions. Preferably, oxygen is supplied with 0 to 3 bar air or oxygen.

Furthermore, additional conditions including the selection of suitable bioreactors or vessels for cultivation of *Bacillus* host cells are well known in the art and can be made by the skilled artisan without further ado.

The term "feed solution" as used herein refers to a solution that is added to the fermentation medium after inoculation of the initial fermentation medium with *Bacillus* host cells. The initial fermentation medium typically refers to the fermentation medium present in the fermenter at the time of inoculation with the *Bacillus* host cells. The feed solution comprises compounds supportive for the growth of said cells. Compared to the fermentation medium the feed solution may be enriched for one or more compounds. Typically, according to the present invention, the feed solution differs from the fermentation medium in one or more compounds. More typically, the feed solution differs from the fermentation medium in at least a compound other than the main carbon source. Even more typically, the feed solution differs from the fermentation medium in at least one of the following compounds selected from the group consisting of a nitrogen source, magnesium salts, sodium salts, calcium salts, potassium salts, salts comprising phosphorus, salts comprising sulfur.

The "main source of carbon" or "main carbon source" typically refers to the carbon source that represents the main source of carbon based on the mass proportions of carbon sources present during cultivation, typically present in the feed solution and/or the initial fermentation medium. The term "carbon source" is typically understood as the compound metabolized by an organism as the source of carbon for building its biomass and/or its growth and/or product formation. Suitable carbon sources include for example organic compounds such as carbohydrates.

A feed medium or feed solution used may typically comprise any of the above mentioned medium components or combination thereof. It is understood herein that at least part of the compounds that are provided as feed solution can already be present to a certain extent in the fermentation medium prior to feeding of said compounds. Preferably, the feed solution comprises a chemically defined carbon source, more preferably the feed solution comprises a chemically defined carbon source as the main carbon source. Even more preferably, the feed solution comprises glucose. More preferably, the feed solution comprises 40% to 60% glucose, preferably 42% to 58% glucose, more preferably 45% to 55% glucose, even more preferably 47% to 52% glucose and most preferably 50% glucose.

A feed solution can be added continuously or discontinuously during the fermentation process. Discontinuous addition of a feed solution can occur once during the fermentation process as a single bolus or several times with different or same volumes. Continuous addition of a feed solution can occur during the fermentation process at the same or at varying rates (i.e., volume per time). Also combinations of continuous and discontinuous feeding profiles can be applied during the fermentation process. Components of the fermentation medium that are provided as feed solution can be added in one feed solution or as different feed solutions. In case more than one feed solution is applied, the feed solutions can have the same or different feed profiles as described above. Particular preferred feed solutions are also described in the Examples below.

The method of the present invention, further preferably, comprises the step of cultivating for a first cultivation phase the *Bacillus* host cell in said fermentation medium under conditions conducive for the growth of the *Bacillus* host cell and the expression of the protein of interest, wherein the cultivation of the *Bacillus* host cell comprises the addition of at least one feed solution and wherein the at least one feed solution provides a carbon source at increasing rates.

The term "first cultivation phase" as used herein refers to a first period of time for which cultivation is to be carried out under addition of at least one feed solution. Said at least one feed solution shall provide a carbon source at increasing rates, preferably exponentially increasing rates. Said period of time may be pre-determined or variable dependent on parameters of the culture, e.g., bacterial growth rates, carbon source consumption rates, amount of carbon source which has been provided to the fermentation medium or the like.

Preferably, said first cultivation phase is carried out for a time of at least about 3 h up to about 48 h, preferably between about 12 h up to about 24 h, preferably for about 22 h. Alternatively, it may be carried out until a pre-determined total amount of carbon source has been provided by the at least one feed solution. Preferably, the at least one feed solution provides a carbon source at exponentially increasing rates with an exponential factor of at least about $0.13\ h^{-1}$, and a starting amount of at least about 1 g per liter and hour of the at least one carbon source. Further preferably, a total amount of at least about 50 g or more of said at least one carbon source per kg *Bacillus* host cell culture being initially present in step b) is added during the first cultivation phase. Further details are to be found in the accompanying Examples, below. The skilled person is well aware of how to determine the time period of the first cultivation phase. The *Bacillus* host cell is cultivated in said first cultivation phase under conditions which allow for the growth of the *Bacillus* host cell and the expression of the protein of interest.

The method of the present invention, also preferably, comprises the step of cultivating for a second cultivation phase the *Bacillus* host cell culture obtained in the previous step under conditions conducive for the growth of the *Bacillus* host cell and the expression of the protein of interest, wherein the cultivation comprises the addition of at least one feed solution and wherein at least one feed solution provides a carbon source at a constant rate, at decreasing rates or at rates increasing less than the rates applied during the first cultivation phase, more preferably, a constant rate.

The term "second cultivation phase" as used herein refers to a second period of time for which cultivation is to be carried out under addition of at least one feed solution. Said at least one feed solution shall provide a carbon source at a constant rate, at decreasing rates or at rates increasing less than the rates applied during the first cultivation phase. Preferably, said constant rate or the starting rate of said decreasing rates or the starting rate of said rates increasing less than the rates in the first cultivation phase is below the maximum rate of the first cultivation phase. Preferably, the degree of increase in the rates of carbon source provided by a feed solution as referred to herein can be determined by comparing individual or constantly applied feed solution amounts and determining, e.g., a factor for the said increase. By comparing the increase factors in the first and second cultivation phase for the carbon source provided by the feed solution, it can be determined whether said carbon source is provided in the second cultivation phase at rates increasing less than in the first cultivation phase. Said second period of time may be predetermined or variable dependent on parameters of the culture, e.g., bacterial growth rates, carbon source consumption rates, amount of carbon source which has been provided to the fermentation medium or the like. In the second cultivation phase there shall be constant growth of the *Bacillus* host cell culture when the at least one feed solution provides a carbon source at a constant rate. Preferably, said second cultivation phase is carried out for a time of at least about 40 h up to about 120 h, preferably at least about 40 h up to about 96 h, preferably for about 68 h. Preferably, the at least one feed solution provides the carbon source at a constant rate Said constant rate, preferably, is maximum feeding rate of carbon source provided by the at least one feed solution during the first cultivation phase. Preferably, it is within the range of about 70% to about 20%, preferably, within the range of about 50% to about 30% or, more preferably, about 35% of the maximum feeding rate for the at least one carbon source applied in the first cultivation phase. The skilled person is well aware of how to determine the time period of the second cultivation period. The *Bacillus* host cell is cultivated in said second cultivation phase under conditions which allow for the growth of the *Bacillus* host cell and the expression of the protein of interest.

In a more preferred embodiment of the method of the invention, thus, said cultivation phase comprises:
 (b1) cultivating for a first cultivation phase the *Bacillus* host cell in said fermentation medium under conditions conducive for the growth of the *Bacillus* host cell and the expression of the protein of interest, wherein the cultivation of the *Bacillus* host cell comprises the addition of at least one feed solution and wherein the at least one feed solution provides a carbon source at increasing rates; and
 (b2) cultivating for a second cultivation phase the *Bacillus* host cell culture obtained in step (b1) under conditions conducive for the growth of the *Bacillus* host cell and the expression of the protein of interest, wherein the cultivation comprises the addition of at least one feed solution and wherein at least one feed solution provides a carbon source at a constant rate, at decreasing rates or at rates increasing less than the rates in step (b1), wherein said constant rate or the starting rate of said decreasing rates or the starting rate of said rates increasing less than the rates in step (b1) is below the maximum rate of the first cultivation phase.

More preferably, said increasing rates in step (b1) are exponentially increasing rates. Also more preferably, said at least one feed solution in step (b2) provides the said carbon source at a constant rate.

Preferably, said cultivation phase in step (c) during which said separating of portions from said *Bacillus* host cell culture at different time points is carried out is the second cultivation phase, only.

In the method of the invention, the separating portions from said *Bacillus* host cell culture are separated from said culture, preferably, during the second cultivation phase, at different time points. This strategy is also referred to herein as "partial harvesting" or "partial harvest strategy". The protein of interest is subsequently obtained from said separated portions.

The separation of said portions is, preferably, carried out by taking samples of the culture having a pre-defined volume. Preferably, the volume to be separated from the *Bacillus* host cell culture is about 40%, about 30%, about 20%, about 15%, about 10%, about 5%, or more preferably about 10%, of the initial volume of *Bacillus* host cell culture. Particularly preferably, the volume to be separated from the *Bacillus* host cell culture lies in the range from about 40% to about 1% of the initial volume of *Bacillus* host cell culture, even more preferably in the range from 30% to 5%, still even more preferably in the range from 20% to 10% of the initial volume of *Bacillus* host cell culture. More preferably, 100 mL *Bacillus* host cell culture are taken per 1 L of initial *Bacillus* host cell culture.

In particular, the partial harvest strategy of the present invention differs from repeated fed-batch cultivation, wherein typically at least 50% of the sum of the initial volume of the host cell culture and the volume of all feeds added to the reactor is removed once or in a repeated manner during the process.

The said portions are to be separated at different time points. Preferably, the portions are separated at at least 2, at least 3, at least 4, or at least 5 different time points during the second cultivation phase. Preferably, said different time points are about 8 h in time apart. Preferably, the separation of *Bacillus* host cell culture starts after about 30 h, about 34 h, about 36 h or, preferably, about 32 h after onset of the second cultivation phase.

After completion of the cultivation phase, the remaining *Bacillus* host cell culture is, preferably, also used as a portion from which the protein of interest is to be obtained.

The protein of interest obtain by the method is, preferably, the combined total protein of interest obtained from all portions. It will be understood that the method of the invention, thus, may also comprise combining the protein of interest obtained in each portion into one preparation.

Preferably, the protein of interest is obtained from the separated *Bacillus* host cell culture portions by purification. Dependent on the nature of the protein of interest, a suitable technique may be selected. For example, if the protein of interest is secreted into the fermentation broth, the *Bacillus* cells may be separated from the culture portions and the protein of interest may be purified from the liquid part of the fermentation broth. If the protein of interest is a cellular protein, i.e. is present within the *Bacillus* host cell, it may be purified by separating the *Bacillus* host cells from the fermentation broth, subsequent lysis of said host cells and purification of the protein of interest from the lysed *Bacillus* host cells of the culture. Alternatively, the *Bacillus* host cells present in the culture after step c) may be lysed and the protein of interest may be purified from the lysed *Bacillus* host cells in the fermentation broth.

Purification of the protein of interest may dependent on the selected technique comprise steps of physical separation, such as centrifugation, evaporation, freeze-drying, filtration (in particular, ultrafiltration) electrophoresis (preparative SDS PAGE or isoelectric focusing electrophoresis) ultra-sound, and/or pressure, or chemical treatments, such as chemical precipitation, crystallization, extraction and/or enzymatic treatments. Chromatography (e.g., ion exchange, hydrophobic, chromatofocusing, and size exclusion chroma-tography) may be applied as well. Affinity chromatography may also be used including antibody-based affinity chroma-tography or techniques using purification tags. Suitable techniques are well known in the art and can be applied depending on the protein of interest by the skilled artisan without further ado.

Moreover, the method of the present invention may also comprise further treatments including treatments of the protein of interest which has been purified as described before. Such treatments may comprise chemical and/or physical treatments which improve the purification such as addition of antifoaming agents or stabilizing agents for the protein of interest. The method of the invention may also encompass manufacturing steps for obtaining a commercial product or article comprising the protein of interest, in particular, capsules, granulates, powders, liquids and the like.

Preferably, the method of the present invention can be used for the manufacture of a purified or partially purified composition comprising the protein of interest. More pref-erably, the method of the present invention provides the protein of interest in purified or partially purified form.

Preferably, the yield of the protein with respect to the glucose consumption rate is significantly increased com-pared to a control. Preferably, said yield is the ratio of the production rate of protein of interest and the glucose con-sumption rate. As a control in this case, the yield of protein of interest can be used which is obtained when carrying out the method of the present invention without partial harvest-ing. More preferably, said yield is increased by at least or up to 10%, 20%, 30%, 40% or 50%.

The increase in yield may be determined dependent on the protein of interest by any technique which allows for spe-cific quantification of the protein of interest. Some tech-niques are referred to elsewhere herein. As referred to herein, said increase is an increase compared to a control. Accordingly, for determining an increase in yield, the pro-duction rates of interest are determined in *Bacillus* host cell culture which has been cultivated according to the method of the present invention and a control *Bacillus* host cell culture. The glucose consumption rates for both cultures are deter-mined and the ratios of the production rate of protein of interest in each culture and the respective glucose consump-tion rate are calculated. Both determined ratios are compared to each other in order to determine an increase in yield as referred to herein. Whether such increase in yield is statis-tically significant, or not, can be determined by various statistical tests well known to those skilled in the art. Typical tests are the Student's t-test or Mann-Whitney U test.

Typically, the temperature during cultivation may be kept constant, preferably, at about 28° C., about 32° C., or more preferably at about 30° C.

In embodiments of the method of the invention where cultivation comprises a first and a second cultivation phase as specified herein, the temperature during cultivation is typically kept constant as well, preferably, at about 28° C., about 32° C., or more preferably at about 30° C.

In a preferred embodiment of the method of the invention, however, said cultivation during the first cultivation phase is carried out at a first temperature and the cultivation during the second cultivation phase is carried out at a second temperature, said second temperature being higher than the first temperature.

The term "first temperature" as referred to herein means a temperature which is used for cultivating the *Bacillus* host cell culture during the first cultivation phase. It will be understood that the first temperature is constantly applied during the first cultivation phase. Moreover, the first tem-perature shall be a temperature which allows for the growth of the *Bacillus* host cell and the expression of the protein of interest. Preferably, said first temperature is within the range of about 28° C. to about 32° C., about 29° to about 31° C. or, preferably, is about 30° C.

The term "second temperature" as referred to herein means a temperature which is used for cultivating the *Bacillus* host cell culture during the second cultivation phase. It will be understood that the second temperature is constantly applied during the second cultivation phase. Moreover, the second temperature shall be a temperature which allows for the growth of the *Bacillus* host cell and the expression of the protein of interest. Preferably, said second temperature is within the range of about 33° C. to about 37° C., about 34° to about 36° C. or, preferably, is about 35° C.

Said second temperature shall be higher than the first temperature. Preferably, said first and said second tempera-ture differ by about 3° C. to about 7° C., about 4° C. to about 6° C., or preferably, by about 5° C.

Preferably, the increase in temperature in the second cultivation phase viz-a-viz the first cultivation phase results in an increase in yield of the protein of interest.

Advantageously, it has been found in the experiments underlying the present invention that when cultivating *Bacil-lus* host cells for the manufacture of a protein of interest, a partial harvest strategy during the cultivation phase was able to significantly increase yield and/or stabilize yield of a protein of interest produced by a *Bacillus* host cell culture compared to control cultures. The beneficial effect on yield was even more increased when the cultivation phase was a two phase cultivation and the partial harvest strategy was carried out during the cultivation phase where a feed solution was providing a carbon source, preferably, glucose, at a constant rate, at decreasing rates or at rates increasing less than the rates in the first cultivation phase where strongly increasing rates, preferably exponentially increasing rates, where applied. In particular, the fermentation without partial harvest reached a normalized maximum product yield on glucose of 1.00 around 45 h after start of fermentation. Thereafter, the yield decreased in a steady fashion to only 0.30 normalized product yield on glucose after 85 h of process time, thus declining in yield by 70% in 40 h. However, the fermentation with partial harvest reached a normalized product yield on glucose of 0.60 around 47 h and reached its maximum yield of 0.62 at 55 h after start of fermentation. After 87 h of fermentation the normalized yield on glucose was still at 0.41, thus declining in yield by 34% in 40 h. Accordingly, a stabilizing effect on yield was demonstrated for the partial harvest strategy. Accordingly, thanks to the present invention, the yield in fermentation processes aiming at the microbiologic production of a protein of interest can be increased by a generally applicable cultivation method. Said method can be easily included into existing production schemes and merely requires the variation of the harvesting strategy; in particular the claimed method allows for optimizing and increasing yield without the need of changing to a continuous production system, which may be laborious and cost-intensive.

The explanations and interpretations of the terms made above apply mutatis mutandis to the embodiments described herein below.

The following embodiments are preferred embodiments of the method of the invention.

In a preferred embodiment of the method of the invention, said cultivation phase comprises:

(b1) cultivating for a first cultivation phase the *Bacillus* host cell in said fermentation medium under conditions conducive for the growth of the *Bacillus* host cell and the expression of the protein of interest, wherein the cultivation of the *Bacillus* host cell comprises the addition of at least one feed solution and wherein the at least one feed solution provides a carbon source at increasing rates; and (b2) cultivating for a second cultivation phase the *Bacillus* host cell culture obtained in step (b1) under conditions conducive for the growth of the *Bacillus* host cell and the expression of the protein of interest, wherein the cultivation comprises the addition of at least one feed solution and wherein at least one feed solution provides a carbon source at a constant rate, at decreasing rates or at rates increasing less than the rates in step (b1), wherein said constant rate or the starting rate of said decreasing rates or the starting rate of said rates increasing less than the rates in step (b1) is below the maximum rate of the first cultivation phase.

In a more preferred embodiment of the method of the present invention, said increasing rates in step (b1) are exponentially increasing rates. More preferably, during the first cultivation phase the at least one feed solution provides a carbon source at exponentially increasing rates with an exponential factor of at least about 0.13 h$^{-1}$, and a starting amount of at least about 1 g per liter and hour of the at least one carbon source. More preferably, during said first cultivation phase a total amount of at least about 50 g of said at least one carbon source per kg *Bacillus* host cell culture being initially present in step b) is added. Preferably, said first cultivation phase is carried out for a time of at least about 3 h up to about 48 h.

In yet a more preferred embodiment of the method of the present invention said at least one feed solution in step (b2) provides the said carbon source at a constant rate. Preferably, said constant rate is the maximum feeding rate provided in the first cultivation phase or is within the range of about 70% to about 20%, preferably, within the range of about 50% to about 30% or, more preferably, about 35% of the maximum feeding rate for the at least one carbon source applied in the first cultivation phase. Preferably, said second cultivation phase is carried out for a time of at least about 40 h up to about 120 h, preferably at least about 40 h up to about 96 h.

In a more preferred embodiment of the method of the present invention, said cultivation phase in step (c) during which said separating of portions from said *Bacillus* host cell culture at different time points is carried out is the second cultivation phase.

In a more preferred embodiment of the method of the present invention, cultivation during the first cultivation phase is carried out at a first temperature and the cultivation during the second cultivation phase is carried out at a second temperature, said second temperature being higher than the first temperature. More preferably, said first and said second temperature differ by about 3° C. to about 7° C., about 4° C. to about 6° C. or, preferably, by about 5° C. More preferably, said first temperature is within the range of about 28° C. to about 32° C., about 29° to about 31° C. or, preferably, is about 30° C. More preferably, said second temperature is within the range of about 33° C. to about 37° C., about 34° to about 36° C. or, preferably, is about 35° C.

In a preferred embodiment of the method of the invention, said *Bacillus* host cell culture is depleted from the at least one carbon source after inoculation of the fermentation medium and prior to the cultivation phase.

In another preferred embodiment of the method of the present invention, the first time point of said different time points in step c) is about 32 h after onset of the cultivation phase.

In a preferred embodiment of the method of the invention, the time difference between said different time points is between 6 h to 10 h, preferably, between 7 h to 9 h or more preferably, about 8 h.

In a preferred embodiment of the method of the present invention, the yield of the protein of interest obtained after step c) is significantly increased compared to a control which has been obtained by carrying out the method of the present invention wherein the protein of interest is obtained after completion of the cultivation phase and wherein no portions of the *Bacillus* host cell culture are separated during the cultivation phase.

In a preferred embodiment of the method of the present invention, said *Bacillus* is selected from the group consisting of: *Bacillus licheniformis*, *Bacillus subtilis*, *Bacillus alkalophilus*, *Bacillus amyloliquefaciens*, *Bacillus brevis*, *Bacillus circulans*, *Bacillus clausii*, *Bacillus coagulans*, *Bacillus firmus*, *Bacillus jautus*, *Bacillus lentus*, *Bacillus megaterium*, *Bacillus pumilus*, *Bacillus stearothermophilus*, *Bacillus thuringiensis*, and *Bacillus velezensis*. More preferably, said *Bacillus* is *Bacillus licheniformis*, *Bacillus pumilus*, or *Bacillus subtilis*, even more preferred *Bacillus* is *Bacillus licheniformis* or *Bacillus subtilis*, and, even more preferably, *Bacillus licheniformis*.

In a still even more preferred embodiment, the host cell belongs to the species *Bacillus licheniformis*, such as a host cell of the *Bacillus licheniformis* strain ATCC 14580 (which is the same as DSM 13, see Veith et al. "The complete genome sequence of *Bacillus licheniformis* DSM 13, an organism with great industrial potential." J. Mol. Microbiol. Biotechnol. (2004) 7:204-211). Alternatively, the host cell may be a host cell of *Bacillus licheniformis* strain ATCC 53926. Alternatively, the host cell may be a host cell of *Bacillus licheniformis* strain ATCC 31972. Alternatively, the host cell may be a host cell of *Bacillus licheniformis* strain ATCC 53757. Alternatively, the host cell may be a host cell of *Bacillus licheniformis* strain ATCC 53926. Alternatively, the host cell may be a host cell of *Bacillus licheniformis* strain ATCC 55768. Alternatively, the host cell may be a host cell of *Bacillus licheniformis* strain DSM 394. Alternatively, the host cell may be a host cell of *Bacillus licheniformis* strain DSM 641. Alternatively, the host cell may be a host cell of *Bacillus licheniformis* strain DSM 1913. Alternatively, the host cell may be a host cell of *Bacillus licheniformis* strain DSM 11259. Alternatively, the host cell may be a host cell of *Bacillus licheniformis* strain DSM 26543.

In a still even more preferred embodiment, the host cell is selected from the group consisting of *Bacillus licheniformis* ATCC 14580, ATCC 31972, ATCC 53757, ATCC 53926, ATCC 55768, DSM 13, DSM 394, DSM 641, DSM 1913, DSM 11259, and DSM 26543.

In a preferred embodiment of the method of the present invention, said expression construct for a gene encoding a protein of interest has been introduced into the *Bacillus* host cell by genetic modification. Preferably, said expression construct comprises one or more heterologous nucleic acids. More preferably, said expression construct is comprised in a vector, preferably, an expression vector.

In another preferred embodiment of the method of the invention, said expression construct comprises nucleic acid sequences endogenously present in said *Bacillus* host cell. Preferably, the expression construct is comprised in the genome of the *Bacillus* host cell. More preferably, said expression construct present in the genome has been genetically modified.

In another preferred embodiment of the method of the invention, said expression construct comprises an expression control sequence which governs expression of the gene encoding the protein of interest in said *Bacillus* host cell. Preferably, said promoter is a constitutively active promoter. Also preferably, said promoter is a heat-insensitive promoter. More preferably, said promoter is selected from the group consisting of: veg promoter, lepA promoter, serA promoter, ymdA promoter, fba promoter, aprE promoter, amyQ promoter, amyL promoter, bacteriophage SPO1 promoter and cryIIIA promoter or a combination of such promoters and/or active fragments or variants thereof.

In a preferred embodiment of the method of the present invention, said fermentation medium is a chemically defined fermentation medium.

In a preferred embodiment of the method of the invention, said fermentation medium comprises macroelements and trace elements in pre-defined amounts.

In a preferred embodiment of the method of the present invention, said at least one feed solution comprises at least one carbon source, preferably, glucose.

In a preferred embodiment of the method of the present invention, said at least one feed solution differs from the fermentation medium in one or more compounds, specified elsewhere herein in further detail.

In a further preferred embodiment of the method of the present invention, said protein of interest is an enzyme. Preferably, said enzyme is a hydrolase (EC 3), preferably, a glycosidase (EC 3.2) or a peptidase (EC 3.4). More preferably, the enzyme is selected from the group consisting of: an amylase, in particular an alpha-amylase (EC 3.2.1.1), a cellulase (EC 3.2.1.4), a lactase (EC 3.2.1.108), a mannanase (EC 3.2.1.25), a lipase (EC 3.1.1.3), a phytase (EC 3.1.3.8), a nuclease (EC 3.1.11 to EC 3.1.31), and a protease (EC 3.4).

The present invention also provides a method for the manufacture of a protein of interest comprising the step of cultivating a *Bacillus* host cell according to the aforementioned method of the present invention and the further step of obtaining the protein of interest from the cultured *Bacillus* host cell.

The present invention also relates to a *Bacillus* host cell culture obtainable by the method of any one of the present invention. Preferably, a *Bacillus* host cell culture in a portion separated during cultivation or the remaining Bacterial host cell culture obtained after separation. It will be understood that the *Bacillus* host cell culture comprises the protein of interest produced by the method of the present invention, preferably, in an increased amount.

The present invention also relates to a composition comprising the protein of interest obtainable by the method of the present invention.

All references cited throughout this specification are herewith incorporated by reference with respect to the specifically mentioned disclosure content and in their entireties.

FIGURES

FIG. 1: Glucose feed rates relative to initial reactor volume for fermentations with either 5.6 g of glucose per L initial volume and without partial harvest (grey dotted line) or 8.8 g of glucose per L initial volume in linear feed phase with partial harvest (black solid line). The arrow indicates the start of feeding at 10 hours after process start.

Figure 2:
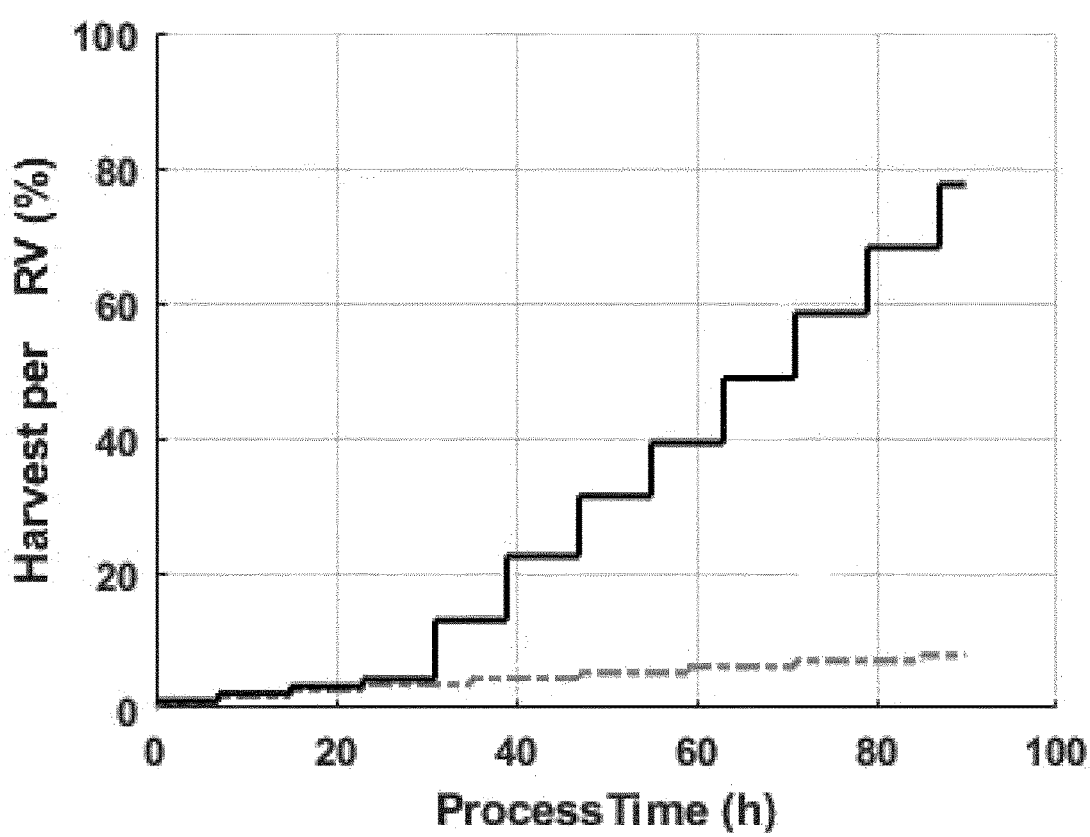

FIG. 2: Time course of mass of harvest per maximum occupied reactor volume (RV) for fermentations without (grey dotted line) and with (black solid line) partial harvest.

Figure 3:
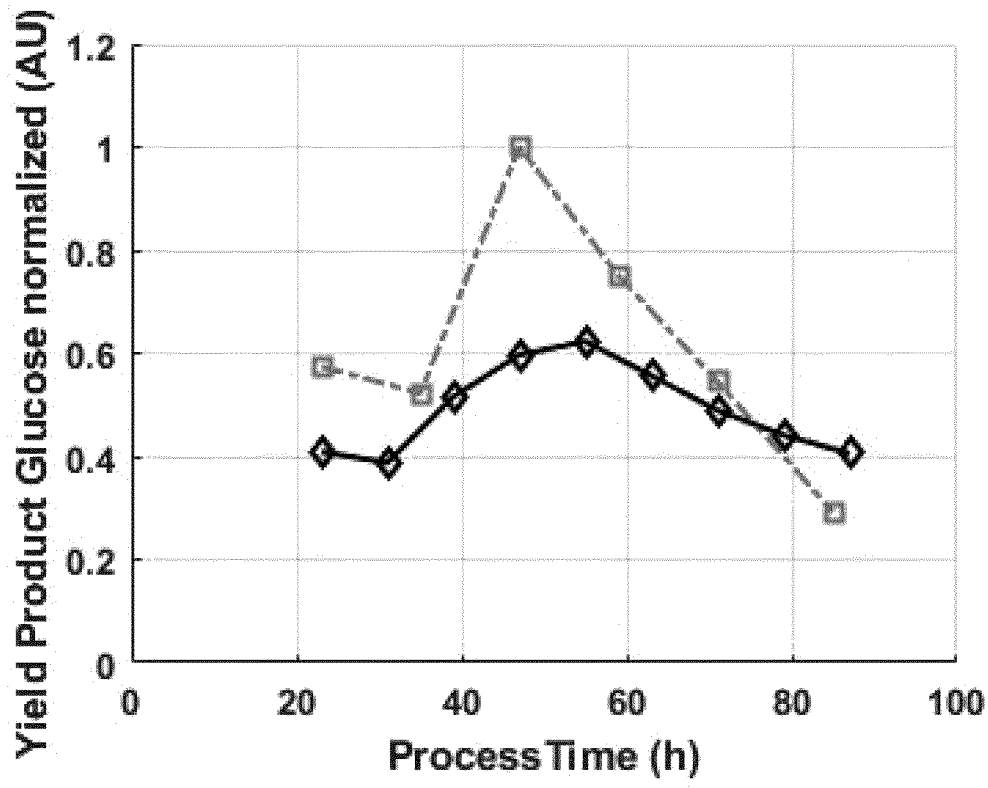

FIG. 3: Time course of normalized yield on glucose for fermentations without (squares) and with (diamonds) partial harvest.

EXAMPLES

The invention will now be illustrated by working Examples. Theses working Examples must not construed, whatsoever, as limitations of the scope of the invention.

Example: Stabilizing Yield of Alkaline Protease 1 on Glucose by Partial Harvest Strategy

*Bacillus licheniformis* strains expressing alkaline protease 1 were cultivated in a fermentation process using a chemically defined fermentation medium providing the components listed in Table 1.

TABLE 1

| Macroelements provided in the fermentation process | | | |
| --- | --- | --- | --- |
| | | Concentration [g/L initial volume] | |
| Compound | Formula | without | with partial harvest |
| Citric acid monohydrate | $C_6H_8O_7$ | 14.3 | 18.8 |
| Calcium sulfate dihydrate | $CaSO_4*2H_2O$ | 1.7 | 2.1 |
| Monopotassium phosphate | $KH_2PO_4$ | 20.5 | 42.1 |
| Disodium phosphate | $Na_2HPO_4$ | 5.3 | 5.3 |
| Magnesium sulfate heptahydrate | $MgSO_4*7H_2O$ | 3.6 | 4.7 |
| Ammonia | $NH_3$ | 26 | 33 |

TABLE 2

| Microelements provided in the fermentation process | | | |
|---|---|---|---|
| | | Concentration [μM initial volume] | |
| Compound | Formula | without | with partial harvest |
| Manganese | Mn | 361 | 499 |
| Zinc | Zn | 266 | 366 |
| Copper | Cu | 498 | 675 |
| Cobalt | Co | 16 | 22 |
| Nickel | Ni | 29 | 40 |
| Molybdenum | Mb | 4 | 6 |
| Iron | Fe | 584 | 806 |

The fermentation was started with a medium containing 8 g/l glucose. A solution containing 50% glucose was used as feed solution. The pH was adjusted during fermentation using ammonia.

The feed was started 10 hours after process start upon depletion of the initial amount of 8 g/l glucose indicated by an increase of culture pH by 0.2 pH units. The glucose feeding strategy consisted of an exponential feed phase with an exponential factor of 0.13 h−1 and a starting value of 1 g of glucose per L initial volume and hour for 22 h. This was followed by a phase of constant glucose feeding with a rate of either 5.6 g or 8.8 g of glucose per L initial volume and hour for 68 h (FIG. 1). In case of the latter a volume of 100 mL per L initial volume was taken as partial harvest every 8 h from 32 h of fermentation time on, whereas in case of the former only minor sampling volumes for analytics were taken (FIG. 2). In both fermentations pH was kept over 7.0 by addition of $NH_4OH$. The cultivation temperature was kept constant at 30° C.

The fermentation without partial harvest reaches a normalized maximum product yield on glucose of 1.00 around 45 h after start of fermentation (FIG. 3). Thereafter, the yield decreases in a steady fashion to only 0.30 normalized product yield on glucose after 85 h of process time, thus declining in yield by 70% in 40 h.

The fermentation with partial harvest reaches a normalized product yield on glucose of 0.60 around 47 h and reaches its maximum yield of 0.62 at 55 h after start of fermentation (FIG. 3). After 87 h of fermentation, the normalized yield on glucose is still at 0.41, thus declining in yield by 34% in 40 h. This indicates clearly a stabilizing effect of the partial harvest strategy on the product yield on glucose.

The invention claimed is:

1. A method for producing a protein of interest from a *Bacillus* host cell comprising the steps of:
(a) inoculating a fermentation medium with a *Bacillus* host cell comprising an expression construct for a gene encoding a protein of interest;
(b1) cultivating for a first cultivation phase the *Bacillus* host cell in said fermentation medium under conditions conducive for the growth of the *Bacillus* host cell and the expression of the protein of interest, wherein the cultivation of the *Bacillus* host cell comprises the addition of at least one feed solution and wherein the at least one feed solution provides a carbon source at increasing rates;
(b2) cultivating for a second cultivation phase the *Bacillus* host cell culture obtained in step (b1) under conditions conducive for the growth of the *Bacillus* host cell and the expression of the protein of interest, wherein the cultivation comprises the addition of at least one feed solution and wherein at least one feed solution provides a carbon source at a constant rate, at decreasing rates, or at rates increasing less than the rates in step (b1), wherein said constant rate or the starting rate of said decreasing rates or the starting rate of said rates increasing less than the rates in step (b1) is below the maximum rate of the first cultivation phase; and
(c) separating portions from said *Bacillus* host cell culture during the cultivation phase at different time points and obtaining the protein of interest from said portions.

2. The method of claim 1, wherein said increasing rates in step (b1) are exponentially increasing rates.

3. The method of claim 2, wherein during the first cultivation phase the at least one feed solution provides a carbon source at exponentially increasing rates with an exponential factor of at least 0.13 h$^{-1}$ and a starting amount of at least 1 g per liter and hour of the at least one carbon source.

4. The method of claim 1, wherein during said first cultivation phase a total amount of at least 50 g of said at least one carbon source per kg *Bacillus* host cell culture being initially present in step b) is added.

5. The method of claim 1, wherein said first cultivation phase is carried out for a time of at least 3 h up to 48 h.

6. The method of claim 1, wherein said at least one feed solution in step (b2) provides the said carbon source at a constant rate.

7. The method of claim 6, wherein said constant rate is within the range of 70% to 20% of the maximum feeding rate for the at least one carbon source applied in the first cultivation phase.

8. The method of claim 1, wherein said second cultivation phase is carried out for a time of at least 40 h up to 120 h.

9. The method of claim 1, wherein said cultivation phase in step (c) during which said separating of portions from said *Bacillus* host cell culture at different time points is carried out is the second cultivation phase.

10. The method of claim 1, wherein cultivation during the first cultivation phase is carried out at a first temperature and the cultivation during the second cultivation phase is carried out at a second temperature, said second temperature being higher than the first temperature.

11. The method of claim 1, wherein, after inoculation of the fermentation medium and prior to the first cultivation phase, the method further comprises depleting at least one carbon source.

12. The method of claim 1, wherein the first time point of said different time points is 32 h after onset of the cultivation phase.

13. The method of claim 1, wherein the time difference between said different time points is between 6 h to 10 h.

* * * * *